United States Patent [19]

Motycka

[11] Patent Number: 4,495,947
[45] Date of Patent: Jan. 29, 1985

[54] HIGH SPEED MEDICAL VENTILATOR

[75] Inventor: Jiri Motycka, Etobicoke, Canada

[73] Assignee: Imasco-CDC Research Foundation, Toronto, Canada

[21] Appl. No.: 421,894

[22] Filed: Sep. 23, 1982

[51] Int. Cl.³ ............................................. A61M 16/00
[52] U.S. Cl. ........................ 128/205.14; 128/204.21; 128/205.18; 417/359; 417/413; 417/45; 417/437; 92/12.2; 92/13.2; 74/839
[58] Field of Search ...................... 128/204.21, 205.13, 128/205.14, 205.15, 205.16, 205.17, 205.18, 28, 30, 30.2, 39, 207.14; 417/222, 359, 212, 53, 413, 500, 45, 437; 92/12.2, 13.2; 74/839, 22 A, 60

[56] References Cited

U.S. PATENT DOCUMENTS

| | | | |
|---|---|---|---|
| 2,155,455 | 4/1939 | Thoma | 74/60 |
| 2,918,917 | 12/1959 | Emerson | 128/204.21 |
| 3,168,872 | 2/1965 | Pinkerton | 417/500 |
| 4,073,603 | 2/1978 | Abendschein et al. | 417/222 |
| 4,155,356 | 5/1979 | Venegas | 128/207.14 |
| 4,215,681 | 8/1980 | Zalkin et al. | 128/205.18 |
| 4,409,977 | 10/1983 | Bisera | 128/205.14 |

FOREIGN PATENT DOCUMENTS

| | | | |
|---|---|---|---|
| 838397 | 7/1949 | Fed. Rep. of Germany | 92/13.2 |
| 2218024 | 10/1973 | Fed. Rep. of Germany | 417/500 |
| 219307 | 1/1942 | Switzerland | 128/30 |

Primary Examiner—Henry J. Recla
Attorney, Agent, or Firm—Bachman and LaPointe

[57] ABSTRACT

A swash plate assembly converts rotary motion to reciprocatory motion to reciprocate a diaphragm in a high frequency medical ventilator; the motor which drives the assembly is pivotally mounted for variation of the stroke of reciprocation thereby varying the tidal volume displaced by the diaphragm.

15 Claims, 2 Drawing Figures

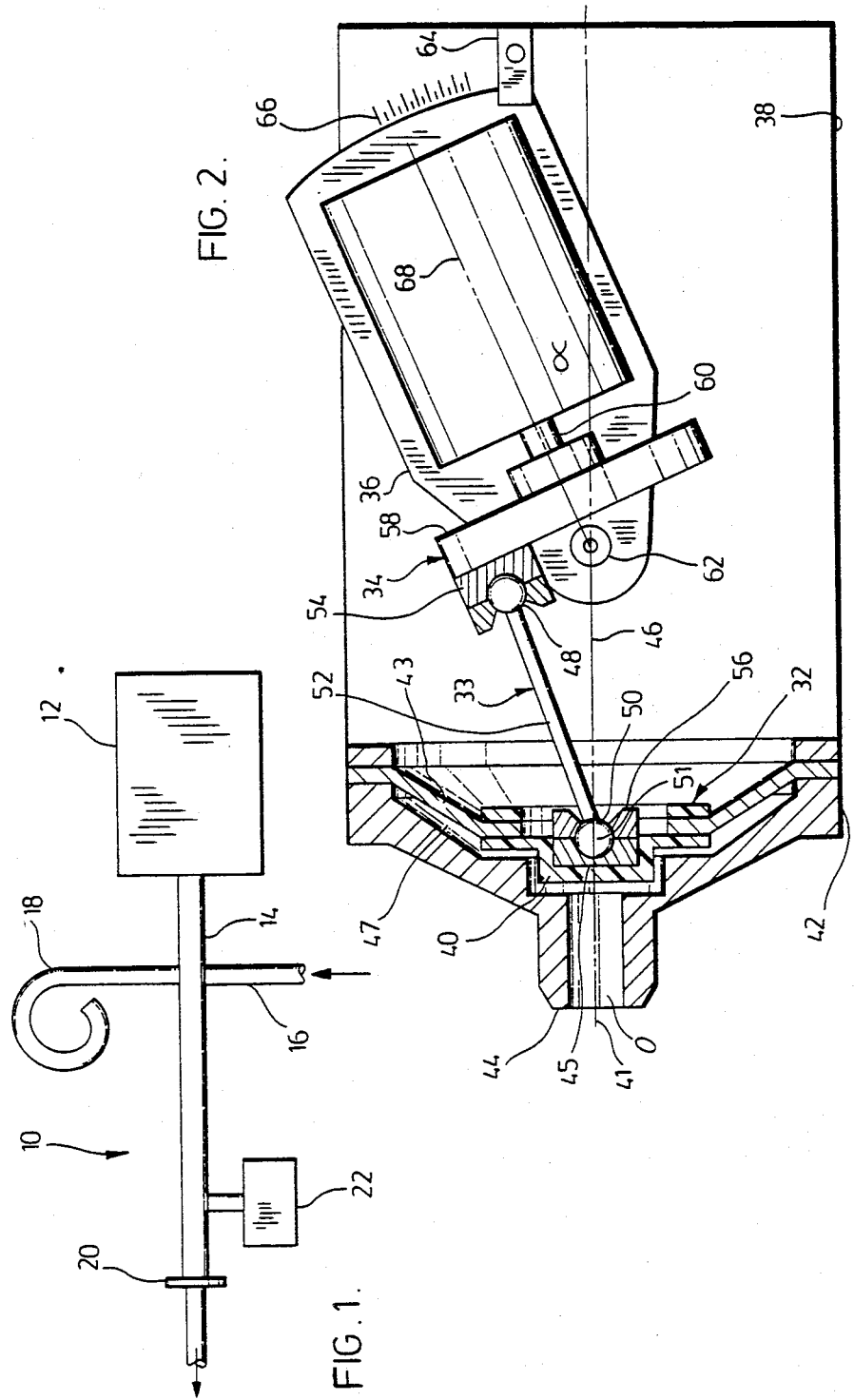

HIGH SPEED MEDICAL VENTILATOR

BACKGROUND OF THE INVENTION (a) Field of the Invention

This invention relates to an apparatus and method for converting rotary motion to reciprocatory motion, and to high frequency medical ventilation.

(b) Description of the Prior Art

High frequency positive-pressure ventilation is a technique for ventilating the lungs and may be used in anaesthesia and in cases of apnoea.

High frequency oscillation of air in the lungs facilitates a high rate of oxygen exchange not only by convection but also by diffusion. In particular the effective diffusion of oxygen arises from the increase in the average air velocity in the lungs.

High frequency ventilation is a comparatively recent development and is described in, for example, a Special Article in Anesthesia and Analgesia, Vol. 59, No. 8, August 1980, pages 567 to 603.

A prior technique for introducing air into the lungs at high frequency involves a valve system which periodically connects the lungs to a pressurized air supply.

SUMMARY OF THE INVENTION

It is an object of this invention to provide a high frequency medical ventilator which provides not only positive insufflation of gas, for example, air to the lungs, but also a subsequent positive withdrawal of air from the lungs.

It is a further object of the invention to provide a high frequency ventilator which effects a sinusoidally variable flow of gas, for example, air, to the lungs, as well as such a ventilator in which both the volume of gas and frequency of ventilation are variable during use.

It is another object of the invention to provide an apparatus for converting rotary motion into reciprocating motion and which can be employed in a high frequency medical ventilator.

It is still another object of the invention to provide a ventilation system incorporating a high frequency ventilator.

It is yet another object of the invention to provide a method of converting rotary motion to reciprocatory motion in which the length of stroke of the reciprocatory motion and optionally the speed of reciprocatory motion can be readily varied, particularly without interrupting the rotary motion.

It is still a further object of the invention to provide a method of producing gas pulsations, particularly high frequency pulsations, and more especially such a method in which the volume of gas being pulsated, and optionally the frequency of the pulsations may be varied as desired.

In accordance with one aspect of the invention there is provided an apparatus for converting rotary motion about a rotary axis to reciprocatory motion along a reciprocation axis comprising: a swash plate assembly including a rotatable shaft and a swash plate mounted on said shaft for rotation therewith, and motor means to rotatably drive said shaft, said motor means being pivotally mounted for variation of the angle of inclination of the rotary axis to the reciprocation axis.

In accordance with another aspect of the invention there is provided a high frequency medical ventilator comprising: a diaphragm mounted in a support frame, swash plate means for converting rotary motion to reciprocatory motion, motor means to drive said swash plate means, and means interconnecting said swash plate means and said diaphragm to transfer reciprocating motion of said swash plate means to said diaphragm.

In accordance with an embodiment of the invention there is provided a medical ventilation system including a medical ventilator of the invention, a tube means for communicating a variable volume chamber adjacent said diaphragm with a body to be ventilated, and a gas inlet means for introducing a ventilating gas into the tube means.

In yet another aspect of the invention there is provided a method of converting rotary motion to reciprocatory motion comprising: rotating a swash plate assembly about a rotary axis to produce a component of reciprocatory motion along a reciprocation axis, said rotary axis being inclined to said reciprocation axis, and varying the angle of inclination of said rotary axis to said reciprocation axis to vary the length of stroke of the reciprocatory motion.

In still another aspect of the invention there is provided a method of producing gas pulsations comprising: rotating a swash plate assembly about a rotary axis to produce a component of reciprocatory motion along a reciprocation axis, and reciprocating a diaphragm with said reciprocatory motion to produce pulsations in a gas volume adjacent said diaphragm.

BRIEF DESCRIPTION OF THE DRAWINGS

The invention is illustrated in a particular and preferred embodiment by reference to the accompanying drawings in which:

FIG. 1 schematically represents a ventilation system, and

FIG. 2 illustrates a medical ventilator of the invention.

DESCRIPTION OF THE PREFERRED EMBODIMENT WITH REFERENCE TO THE DRAWINGS

With further reference to FIG. 1 there is shown a medical ventilation system 10 comprising a medical ventilator 12, a gas conduit 14, a gas inlet passage 16, a low pass filter 18, a flow meter 20 and a humidifer 22.

In operation gas, for example, air is introduced into gas conduit 14 through gas inlet passage 16 and a pulsating flow is applied to the gas by the medical ventilator 12.

Humidifer 22 humidifies the gas as desired.

Gas conduit 14 suitably terminates in the lungs of a patient, for introduction of the gas thereto.

Flow meter 20 permits monitoring of the amount of gas and the rate of introduction whereby the ventilator 12 can be adjusted with respect to one or both of the volume and the frequency of the pulsations of gas.

The medical ventilator 12 provides both a positive insufflation of the gas as well as a subsequent positive withdrawal of gas from the lungs. Typically the ventilator 12 may operate at 20–40 cycles per second.

The low pass filter 18 permits passage of gas during spontaneous breathing of the patient as well as exhaust of gas, but provides a high resistance to high frequency pulsations of gas developed by the ventilator 12.

With further reference to FIG. 2 a medical ventilator 30 comprises a diaphragm assembly 32, a ball joint bearing assembly 33, a swash plate assembly 34 and a motor 36, all mounted on a platform 38.

Diaphragm assembly 32 includes a diaphragm 40 having a central axis 41. Diaphragm 40 is of a generally circular configuration and is sealingly mounted at its outer circumferential edge in a stationary support frame 42 which includes a conduit 44 disposed about the reciprocation axis 46 of diaphragm 40.

A chamber 47 is defined between diaphragm 40 and frame 42.

Ball joint bearing assembly 33 comprises spherical bearings 48 and 50 connected by a rod 52. Spherical bearing 50 has a center 51.

Bearings 48 and 50 are bearingly mounted in bearing houses 54 and 56 respectively.

Swash plate assembly 34 includes a swash plate 58 mounted for rotation with a shaft 60.

Motor 36, which is in particular a DC motor, is pivotally mounted about pivot 62 on the reciprocation axis 46 to drive the shaft 60.

Shaft 60 has a rotary axis 68 inclined to reciprocation axis 46 by an angle $\alpha$. The angle $\alpha$ can be adjusted by pivoting motor 36 about pivot 62.

A locking member 64 locks motor 36 at a desired angle of inclination $\alpha$.

A scale 66 is calibrated to identify the volume of pulsations delivered by ventilator 30 for different angles of inclination $\alpha$.

A central portion of diaphragm 40 is secured to bearing housing 56 such that the centre 51 of spherical bearing 50 lies on the central axis 41 of diaphragm 40; the central axis 41 also coincides with the reciprocation axis 46.

Bearing housing 54 is mounted on swash plate 58 for rotation therewith.

In use, tubing such as gas inlet passage 16 in FIG. 1 is connected to conduit 14 for delivery of the pulsations developed by ventilator 30.

It will be understood that diaphragm 40 should be sealingly mounted in frame 42 so as to be gas tight.

In operation motor 36 is pivoted about pivot 62 to a particular angle of inclination $\alpha$ to give a desired volume of gas to be pulsed, the setting being determined by reference to scale 66.

The motor 36 rotatably drives shaft 60 with swash plate 58 and bearing housing 54. As swash plate 58 rotates, the distance between bearing housing 58 and frame 42 varies cyclically; since rod 52 is of a fixed length, bearing 50 with bearing housing 56 is reciprocated, and diaphragm 40, secured to housing 56, is likewise reciprocated.

It will be understood that a particular angle of inclination $\alpha$ determines the volume, or variation thereof, of chamber 47 and also the length of stroke of the reciprocatory motion. If the angle of inclination $\alpha$ is altered, as hereinbefore described, the volume of chamber 47 is altered accordingly.

Consequently the volume of the pulsations of gas can be altered by altering the volume of chamber 47. This alteration can be carried out during operation, but it is not, for example, necessary to stop or otherwise interrupt the motor to effect the alteration.

By increasing or decreasing the speed of rotation of the shaft 60, for example, by an appropriate adjustment of motor 36 or related gearing (not shown), the frequency of the pulsations can also be altered. This step can also be carried out during the operation and it is not necessary to stop or otherwise interrupt the rotation of shaft 60.

Consequently it can be seen that by pivoting motor 36 about pivot 62 the volume of chamber 47 and the effective displacement of diaphragm 40 can be modified and therefore the tidal volume developed by ventilator 30 can be adjusted as desired.

The ventilator 30 thus both supplies gas, for example, air into the lungs and withdraws gas during each cycle; the gas being supplied in a sinusoidally variable flow.

The ventilator 30 is of simple structure and can be easily cleaned and sterilized. In addition it may be readily built from materials compatible with the intended clinical use.

The diaphragm 40 may be fabricated of any appropriate material for example, of stretch rubber or plastic material and suitably may contain permanently formed concentric grooves to facilitate flexing for the axial displacement.

By disposing the central axis 41 of diaphragm 40 and the centre 51 of spherical bearing 50 along the reciprocation axis 46, the formation of undesired oscillatory modes in the diaphragm 40 can be substantially minimized.

In the embodiment schematically illustrated in FIG. 2, the pivot 62 of motor 36 is on the central axis of the motor 36. It is also possible to provide pivot 62 so that it is offset or disposed to one side of the axis of the motor 36 so as to keep the dead space of chamber 47 at a minimum for any tidal volume. When pivot 62 is offset relative to the central axis of the motor 36, the diaphragm 40 vibrates not around its central unloaded position but in such a way that there is a minimum dead space for any effective eccentricity.

Since the ball joint bearing assembly 53 will require lubrication from time to time between bearings 48 and 50 in their respective housings 54 and 56, it is appropriate to provide a lubricant cavity for a grease or semi-solid lubricant, and connecting passages in the rod 52 to the bearing housings 54 and 56.

The diaphragm 40, as shown in FIG. 2 comprises an annular diaphragm member 43, suitably of rubber, and a mounting 45 for bearing housing 56. Mounting 45 engages the inner circumferential edge of annular member 43. The outer circumferential edge of annular member 43 is retained in support frame 42.

The medical ventilator 30, in accordance with the invention is employed to create an oscillatory air flow with a frequency variable, of for example, 0 to 60 Hz and a tidal volume variable from 0 to 250 ml.

I claim:

1. Apparatus for converting rotary motion about a rotary axis to reciprocatory motion along a fixed reciprocation axis inclined to said rotary axis comprising:
    a support means defining a longitudinally extending reciprocating axis,
    a motor having an output shaft rotatable about a longitudinally extending rotary axis, a swash plate mounted on said output shaft, said swash plate being mounted normally to said output shaft,
    a reciprocatible element mounted on said support means to reciprocate along said reciprocating axis, linkage means for interconnecting said swash plate with said reciprocating element and having opposite ends, said swash plate having first connector means eccentrically mounted thereto and rotatable in a plane parallel to said swash plate, one end of said linkage means being connected to said first connector means, said reciprocating element having second connector means mounted centrally thereof, the opposite end of said linkage means being connected to said second connector means, said first and second connector means permitting universal movement of said opposite ends therewith whereby a component of reciprocating motion developed at said swash plate is transferred to said reciprocating element, and said motor being pivotally mounted to said support means about a pivot located at the intersection of said reciprocating axis and the plane in which said first connector rotates such that pivoting said motor pivots said swash plate and shaft as a unit and varies the angle of inclination of the rotary axis to the reciprocating axis.

2. Apparatus according to claim 1, including locking means for locking the pivotally mounted motor means at a desired angle of inclination.

3. Apparatus according to claim 1, wherein said motor means is pivotally mounted about said reciprocation axis.

4. Apparatus according to claim 1 wherein said reciprocatible element comprises ball joint means comprising first and second spherical bearings and a rod connecting said bearings; a first bearing housing mounted on said swash plate for rotation therewith and a second bearing housing adapted to be secured to a member to be reciprocated along said fixed reciprocation axis, said first bearing being bearingly mounted in said first bearing housing, and said second bearing being bearingly mounted in said second bearing housing.

5. Apparatus according to claim 4, including a cavity for lubricant in said rod, and passages for flow of lubricant from said cavity to said spherical bearings.

6. A high frequency medical ventilator for converting rotary motion about a rotary axis to reciprocatory motion along a fixed reciprocation axis inclined to said rotary axis comprising:

a support frame defining a longitudinally extending reciprocating axis, a motor having an output shaft rotatable about a longitudinally extending rotary axis, a swash plate mounted on said output shaft, said swash plate being mounted normally to said output shaft, a chamber mounted on said support frame having an open end and outlet means adapted to be connected to patient breathing circuitry, a reciprocating diaphragm for establishing ventilation mounted on said open end, said chamber being oriented such that said diaphragm reciprocates along said reciprocating axis, linkage means for interconnecting said swash plate with said reciprocating diaphragm and having opposite ends, said swash plate having first connector means eccentrically mounted thereto and rotatable in a plane parallel to said swash plate, one end of said linkage means being connected to said first connector means, said reciprocating diaphragm having second connector means mounted centrally thereof, the opposite end of said linkage means being connected to said second connector means, said first and second connector means permitting universal movement of said opposite ends therewith whereby a component of reciprocating motion developed at said swash plate is transferred to said reciprocating diaphragm, and said motor being pivotally mounted to said support means about a pivot located at the intersection of said reciprocating axis and the plane in which said first connector rotates such that pivoting said motor pivots said swash plate and shaft as a unit and varies the angle of inclination of the rotary axis to the reciprocating axis, said linkage means comprising ball joint means including a first bearing housing connected to said swash plate for rotation therewith, and a second bearing housing connected to said diaphragm for reciprocatory motion therewith and first and second spherical bearings being connected by a rod, said first spherical bearing being bearingly mounted in said first bearing housing, and said second spherical bearing being bearingly mounted in said second bearing housing.

7. A medical ventilator according to claim 6, including locking means for locking the pivotally mounted motor means at a desired angle of inclination.

8. A medical ventilator according to claim 1, wherein said diaphragm is of stretchable rubber.

9. A medical ventilator according to claim 6, wherein said diaphragm is secured to said second bearing housing, such that the centre of the second spherical bearing, the centre of the diaphragm and the reciprocation axis all lie in a single plane.

10. A medical ventilation system for converting rotary motion about a rotary axis to reciprocatory motion along a fixed reciprocation axis inclined to said rotary axis comprising:

a support frame defining a longitudinally extending reciprocating axis, a motor having an output shaft rotatable about a longitudinally extending rotary axis, a swash plate mounted on said output shaft, said swash plate being mounted normally to said output shaft, a chamber mounted on said support frame having an open end and outlet means adapted to be connected to patient breathing circuitry, a reciprocating diaphragm for establishing ventilation mounted on said open end, said chamber being oriented such that said diaphragm reciprocates along said reciprocating axis, ball joint bearing linkage means for interconnecting said swash plate with said reciprocating diaphragm and having opposite ends, said swash plate having first connector means eccentrically mounted thereto and rotatable in a plane parallel to said swash plate, one end of said linkage means being connected to said first connector means, said reciprocating diaphragm having second connector means mounted centrally thereof, the opposite end of said linkage means being connected to said second connector means, said first and second connector means permitting universal movement of said opposite ends therewith whereby a component of reciprocating motion developed at said swash plate is transferred to said reciprocating diaphragm, and said motor being pivotally mounted to said support means about a pivot located at the intersection of said reciprocating axis and the plane in which said first connector rotates such that pivoting said motor pivots said swash plate and shaft as a unit and varies the angle of inclination of the rotary axis to the reciprocating axis, tube means adapted to communicate said chamber with a body to be ventilated and gas inlet means for introducing a ventilating gas into said tube means.

11. A ventilation system according to claim 6, further including flow meter means in said tube means for monitoring flow of gas in said tube means.

12. A ventilation system according to claim 6, further including a low pass filter communicating with said tube means, adapted to permit passage of gas during spontaneous breathing and providing a high resistance to high frequency pulsations of gas.

13. A ventilation system according to claim 10, including locking means for locking the pivotally mounted motor at a desired angle of inclination.

14. A ventilation system according to claim 13, wherein said ball joint bearing means comprises first and second spherical bearings connected by a rod, said first bearing being bearingly mounted in a first bearing housing and said second bearing being bearingly mounted in a second bearing housing, said first bearing housing being eccentrically mounted for rotation with said swash plate and said diaphragm being secured to said second bearing housing.

15. A ventilation system according to claim 14, wherein said diaphragm is secured to said second bearing housing, such that the centre of the second spherical bearing, the centre of the diaphragm and the reciprocation axis all lie in a single plane.

* * * * *